(12) United States Patent
Bullivant et al.

(10) Patent No.: US 6,322,494 B1
(45) Date of Patent: Nov. 27, 2001

(54) ENDOSCOPE

(75) Inventors: Jarrett Bullivant, Oxfordshire; Robert William Goddard, Pontypridd, both of (GB)

(73) Assignee: Gyrus Medical Limited, Cardiff (GB)

( * ) Notice: Subject to any disclaimer, the term of this patent is extended or adjusted under 35 U.S.C. 154(b) by 0 days.

(21) Appl. No.: 09/271,917

(22) Filed: Mar. 18, 1999

(30) Foreign Application Priority Data

Apr. 3, 1998 (GB) .................................................. 9807302

(51) Int. Cl.$^7$ .................................................. A61B 1/018
(52) U.S. Cl. .............................. 600/104; 600/105; 606/48
(58) Field of Search .................................... 600/104–106, 600/154; 606/41, 46, 47, 48

(56) References Cited

U.S. PATENT DOCUMENTS

| | | | |
|---|---|---|---|
| 4,653,476 | * | 3/1987 | Bonnet .................................. 600/106 |
| 5,007,907 | | 4/1991 | Nishigaki et al. . |
| 5,697,909 | | 12/1997 | Eggers et al. . |
| 5,797,835 | * | 8/1998 | Green .................................... 600/106 |

FOREIGN PATENT DOCUMENTS

| | | |
|---|---|---|
| 2 156 222 | 10/1985 | (GB) . |
| 2 307 644 | 6/1997 | (GB) . |
| WO 98/07377 | 2/1998 | (WO) . |

* cited by examiner

Primary Examiner—John P. Leubecker
(74) Attorney, Agent, or Firm—Nixon & Vanderhye, P.C.

(57) ABSTRACT

An endoscope comprises a telescope (12), an electrode assembly (13) comprising at least one electrode (13T), and elongate conductive means (13S) for supplying electrosurgical power to said at least electrode from the proximal end of the conductive means. Means are provided for supporting the electrode assembly (13) on the telescope (12) for pivotal movement, in a plane substantially normal to the axis of the telescope, towards, and away from, an operational position in which the conductive means (13S) is substantially parallel to the telescope. Sealing means (16,29) seals the electrode assembly (13) to prevent fluid passing from an operation site adjacent to said at least one electrode (13T) to the proximal end of the conductive means (13S).

11 Claims, 3 Drawing Sheets

ENDOSCOPE

BACKGROUND OF THE INVENTION

This invention relates to a endoscope for use in, for example, endoscopic urological surgery, and in particular to a resectoscope for use with an electrosurgical instrument.

In International Patent Applications Nos. WO 97/00647, WO 97/24994, WO 97/24993, WO 97/00646, WO 97/48345 and WO 97/48346, the applicants disclose a number of bipolar electrode assemblies for mounting on the distal end of an elongate tubular instrument shaft. In each case, the electrode assembly is designed for operation whilst immersed in a conductive liquid, typically normal saline, through which current flows from a tissue treatment electrode placed on, or adjacent to, tissue to be treated, to a return electrode which is spaced back from the tissue treatment electrode away from the tissue surface. An electrosurgical generator suitable for supplying power to the disclosed electrode assemblies is described and shown in the applicants' European Patent Application No. EP 0754437. This generator provides for different modes of operation, a first mode being a tissue desiccation or coagulation mode in which the peak voltage applied between the electrodes is limited to prevent vapour pocket formation at the tissue treatment electrode, and a second mode in which tissue is vaporised to produce a cutting or bulk removal effect at an operation site. During the second mode, the power supplied to the electrode assembly causes the formation, from the conductive liquid, of a vapour pocket around the tissue treatment electrode. In this case, the peak voltage applied to the electrode is limited to control the size of the vapour pocket and to prevent electrode destruction. A third mode of operation is a blended mode achieved by switching between the electrical conditions for the first and second modes.

The full subject matter of the above-mentioned applications is incorporated in this specification by reference.

Such an electrode assembly is typically introduced into body cavity through the working channel of an endoscope inserted through a natural body orifice or through a separate aperture formed to obtain access to the cavity. In either circumstance, the tubular instrument shaft provides the return path for electrosurgical currents, connection to the tissue treatment electrode being made through an insulated conductor passing through the shaft interior. The tubular member also provides for heat transfer away from the electrodes during operations. Thermal dissipation from the electrodes is enhanced by a portion of the shaft being immersed in the conductive liquid.

Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site. A gaseous medium is commonly employed when endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electrode. A resectoscope is an endoscope specifically adapted to include means for mounting an electrode.

Endoscopic urological surgery is performed routinely to treat pathologies of the urinary tract, using a range of sophisticated instruments introduced through the urethra. Resectoscopes are a specific form of endoscope originally developed for urological surgery. They have since been used in hysteroscopic and gastrointestinal surgery for removal of soft tissues. Resectoscopes differ from many other endoscopes in that they include an integral trigger mechanism to produce a controlled forwards and backwards motion of an instrument attached to the mechanism. This control is particularly useful during removal of large volumes of tissue. As such, it is the instrument of choice for performing transurethral prostatectomy (TURP), the removal of a benign overgrowth of the prostate gland, endometrial and fibroid resection during hysteroscopic surgery, and the resection of polyps and tumours in the rectum during endoscopic gastrointestinal surgery.

Irrigating solutions may be delivered by continuous or intermittent flow through the resectoscope, and may be electrolyte or non-electrolyte based. As the traditional technique for performing TURP is monopolar electrosurgery, a non-electrolyte is most commonly used. Conventional instruments, therefore, comprise a range of monopolar electrodes mounted on the resectoscope.

Current resectoscopes are designed for use with monopolar electrodes. Essentially, this form of electrosurgery uses an electrode to supply current to the operating site, and to a patient earth plate to complete the circuit. Since the body is earthed, the procedure is carried out in a non-conductive fluid medium that prevents arcing away from the operative site.

As shown in FIG. 1, the known type of resectoscope consists of four main components, an inner sheath 1, an outer sheath 2, a rod lens telescope/light source assembly 3, a working element, indicated generally by the reference W, to the right of the dotted line shown in FIG. 1, and a monopolar electrode (not shown).

The sheaths 1 and 2 provide for the supply and aspiration of an operating site with a fluid medium via a connector 3a. The outer sheath 2 locks over the inner sheath 1, forming a watertight seal. Typically, the inner sheath 1 has a diameter of 24Fr, and the outer sheath 2 has a diameter of 27 Fr. The telescope assembly 3 provides the means of illuminating and viewing the operative site via a light source (not shown) connected thereto by a connector 4. The viewing angle of the telescope is generally at 30° to its axis.

The working element W may be either passive or active, that is to say the cutting stroke of the electrode may be as the result of a spring bias or against the force of a spring bias. The telescope assembly 3 includes a telescope support tube, T having a telescope connector 5 at its proximal end, and a sealing block 6 located part way there along, the inner sheath 1 being connected to the sealing block. Both of these interfaces are watertight. An electrode support tube 7 is attached to the underside of the telescope support tube T on the distal side of the sealing block 6 for the majority of its length. Two spring-loaded links 8 and an insulation block 9, located between the sealing block 6 and the telescope connector 5, make up the mechanism. The active mechanism is arranged so that the spring-loaded links 8 assist the forward stroke, while, in the passive version the links aid the backward stroke. In general, the range of travel is about 25 mm.

The sealing block 6 has a hole through it to allow the telescope support tube T to be passed from the proximal to the distal end of the working element W, within the bore of the inner sheath 1. This hole is offset, so that the telescope is located in the upper quadrate of the inner sheath aperture to make room for the electrode support tube 7.

The monopolar electrode can be inserted down the electrode support tube 7 from the distal end thereof, and through a second hole in the sealing block 6. This hole is angled, so that the electrode exits the sealing block 6 at an increased distance from the telescope support tube T. This is necessary so the electrode can pass into the insulation block 9 with sufficient insulating material ($\geq 1.0$ mm) being present between the electrode and the telescope support T to provide electrical isolation.

The need to bend the electrode shaft through the sealing block 6 inevitably increases the level of friction, and requires that the electrode shaft is very flexible. In addition, the diameter of that part of the electrode shaft which passes through the sealing block 6 is restricted to a maximum size of 2 mm.

The electrode is made watertight by a seal located in the sealing block 6. This seal is subject to wear, and is easily damaged. To compensate for this, an adjustment feature deforms the seal to maintain performance. Adjustment is not, however, possible when an electrode is fitted, so can only be carried out between procedures. The seals are prone to leak, and are generally replaced when the leakage becomes excessive.

The insulation block 9 contains a mechanism that grips the electrode shaft. While providing mechanical retention of the electrode, the mechanism is also the electrical connection to an electrical supply lead (not shown) via a connection socket 10 located on top of the insulation block 9. The block body is made of a non-conductive material to isolate the electrical path from the other parts of the resectoscope. PTFE is generally used, because it offers very low resistance to sliding.

This type of resectoscope has only been a practical proposition for monopolar electrode configurations. This is because the insulation block is of limited size, and would need to support two electrical conductors for a bipolar assembly, and these conductors would need to be spaced sufficiently apart from one another (and from the telescope tube) to ensure good electrical isolation. In practice, this is not possible with the known type of resectoscope, because both conductors must pass through a 2 mm aperture at the proximal end of the electrode support tube 7.

The difficulties of loading a bipolar electrode assembly into a resectoscope in the accepted way centre on the need to ensure electrical isolation within the insulation block. Whilst sufficient creep and air clearances can be achieved, the possibility of conductive fluid penetrating the block and causing a short circuit exists. This can occur during use if the shaft seal leaks, or during drainage of irrigation solution from a body cavity.

OBJECTS AND SUMMARY OF THE INVENTION

The aim of the invention is to provide means for mounting an electrode assembly (and in particular a bipolar electrode assembly) with integral electrical connection to an electrosurgical generator, such that the risks of short circuit with the resectoscope, or as a result of fluid leaks, are minimised. It is a further aim of the invention to provide a sealing mechanism which reduces fluid leakage through the instrument channel of the resectoscope during use.

The present invention provides an endoscope comprising a telescope, an electrode assembly comprising at least one electrode and elongate conductive means for supplying electrosurgical power to said at least one electrode from the proximal end of the conductive means, mounting means for supporting the electrode assembly on the telescope for pivotal movement, in a plane substantially normal to the axis of the telescope, towards, and away from, an operational position in which the conductive means is substantially parallel to the telescope, and sealing means for sealing the electrode assembly to prevent fluid passing from an operation site adjacent to said at least one electrode to the proximal end of the conductive means.

Advantageously, the sealing means is constituted by a seal attached to the conductive means, and a sealing block associated with the telescope, the sealing block being formed with a slot for receiving the seal. Preferably, the seal has the tapering cross-section, and the slot in the sealing block is of complementary shape, whereby the seal forms a sliding friction fit within the slot of the sealing block. The electrode assembly is subsequently movable longitudinally relative to the seal, whilst ensuring good watertight sealing against fluid flow towards said proximal end of the conductive means.

In a preferred embodiment, the electrode assembly comprises a tissue treatment electrode and a return electrode, and the elongate conductive means is constituted by a pair of conductors. Conveniently, each of the conductors is an insulation-coated, spring steel conductor.

Preferably, the proximal ends of the conductors terminate in an electrical connector. The electrical connector may include electrical connection means for connecting the conductors to an electrosurgical generator by a flying lead and an in-line connector, and preferably it is a watertight unit.

Advantageously, the mounting means includes a mounting block associated with the telescope, and means fixed to the electrode assembly for engagement with the mounting block In this case, the mounting block may be formed with a curved recess for receiving a complementary curved surface of the electrical connector, whereby the electrical connector is rotatable relative to the mounting block so that the electrode assembly can be pivoted into its operational position.

Conveniently, the mounting means firther comprises a clip fixed to the conductive means at the distal end portion thereof, the clip being adapted for engagement with the distal end portion of the telescope.

Whilst primarily intended to facilitate use of a bipolar system, the invention is also compatible with monopolar systems, offering the benefits of improved sealing and electrical integrity.

BRIEF DESCRIPTION OF THE DRAWINGS

The invention will now be described in greater detail, by way of example, with reference to the drawings, in which.

DETAILED DESCRIPTION OF THE PREFERRED EMBODIMENTS

Figure 1:
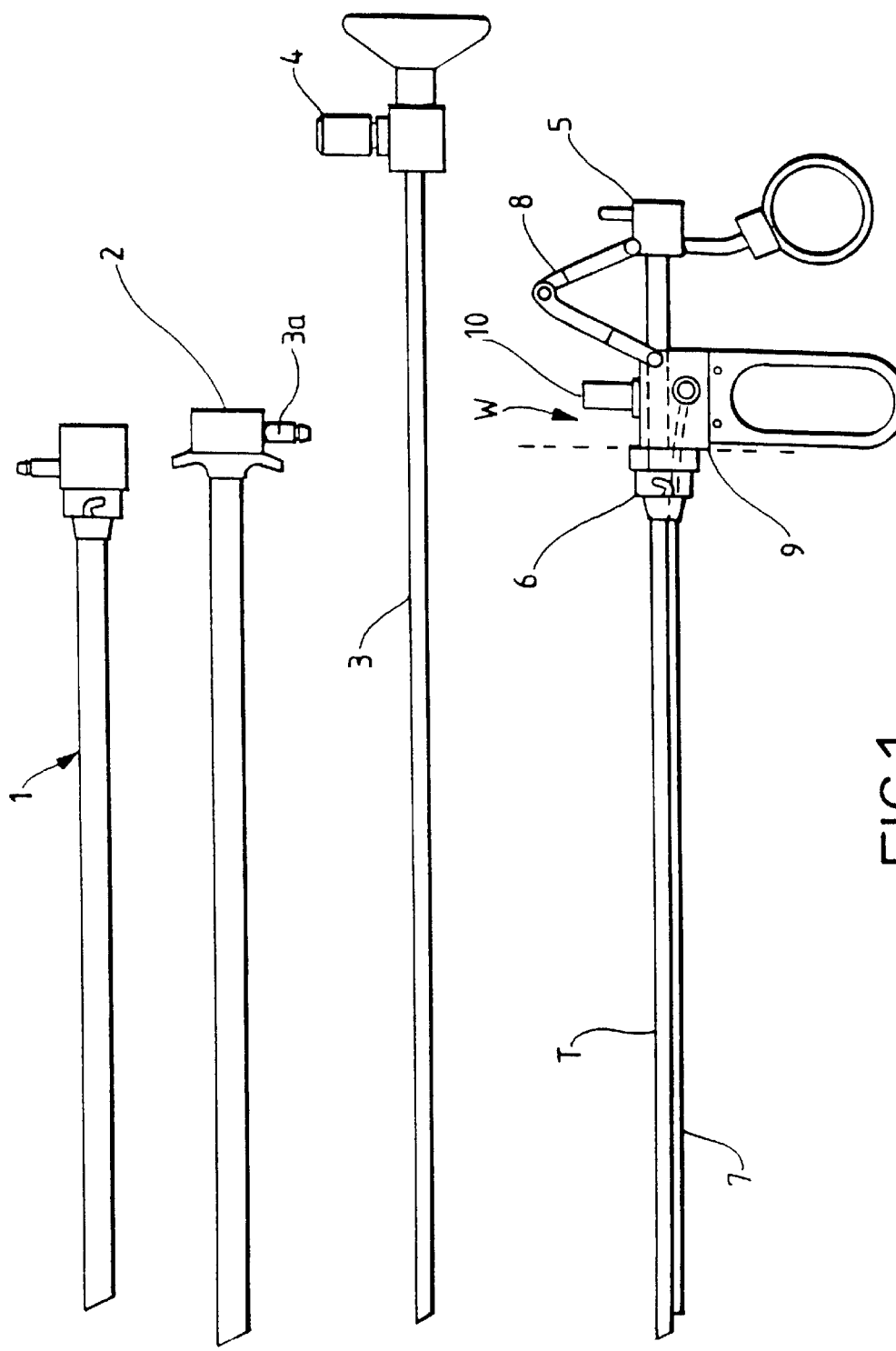
FIG. 1 is an exploded perspective view of a prior art resectoscope.
Figure 2A:
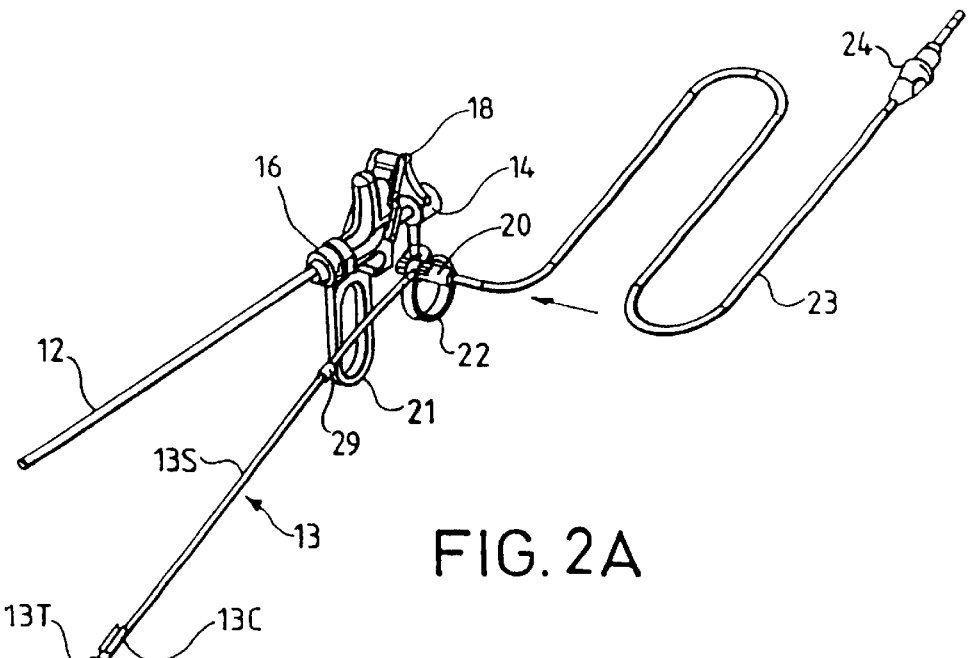
FIGS. 2A, 2B and 2C are perspective views of a resectoscope constructed in accordance with the invention, the resectoscope being shown in three different stages of assembly.
Figure 2B:
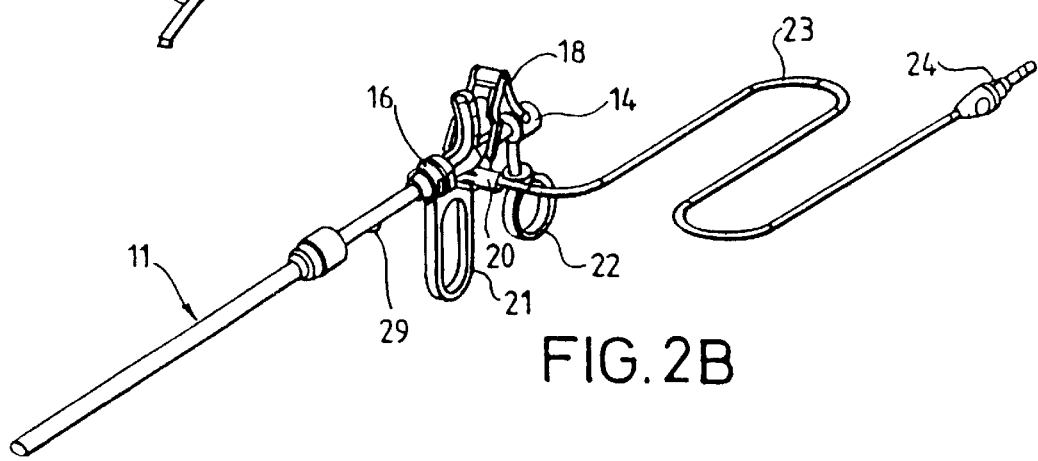
Figure 2C:
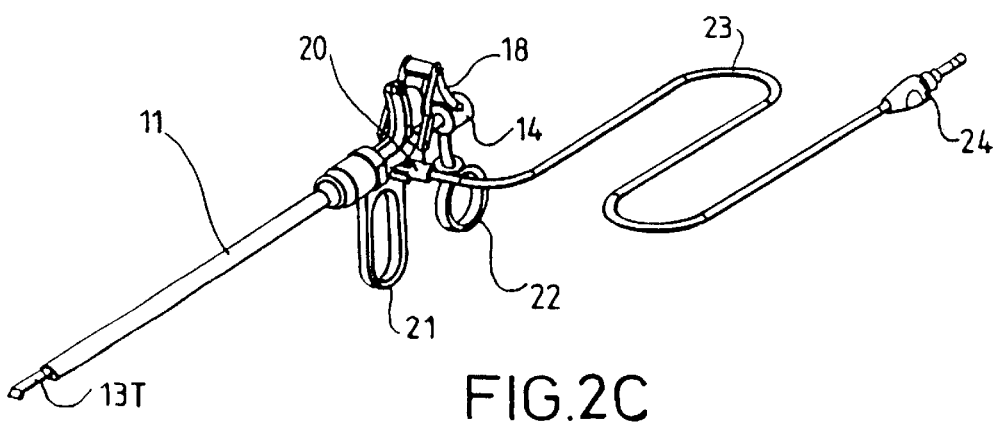

Referring to the drawings, FIGS. 2A to 2C show a resectoscope incorporating a bipolar electrode assembly. Thus, the resectoscope consists of four main components, an inner sheath 11, an outer sheath (not shown), a telescope/light source assembly (only the support tube 12 of which can be seen), and a bipolar electrode assembly 13. The electrode assembly 13 has an elongate support structure 13S supporting a distal electrode tip 13T which includes a tissue treatment electrode and a return electrode. The support structure 13S takes the form of a pair of insulatively-sleeved, spring steel, wire conductors which, towards their distal ends, carry a spring clip 13C for securing the electrode assembly 13 to the telescope tube 12, in such a way that the electrode assembly may be reciprocated distally and proximally with the clip 13C sliding on the tube.

The two sheaths provide for the supply and aspiration of an operation site with a fluid medium. The outer sheath locks over the inner sheath 11, forming a watertight seal., and is provided with an inlet port for connection to a fluid medium source. Typically, the inner sheath 11 has a diameter of 24Fr, and the outer sheath has a diameter of 27 Fr. The telescope assembly provides the means of illuminating and viewing the operative site via a light source (not shown) connected thereto by a connector 14. The viewing angle of the telescope is generally at 30° to its axis.

Figure 3:
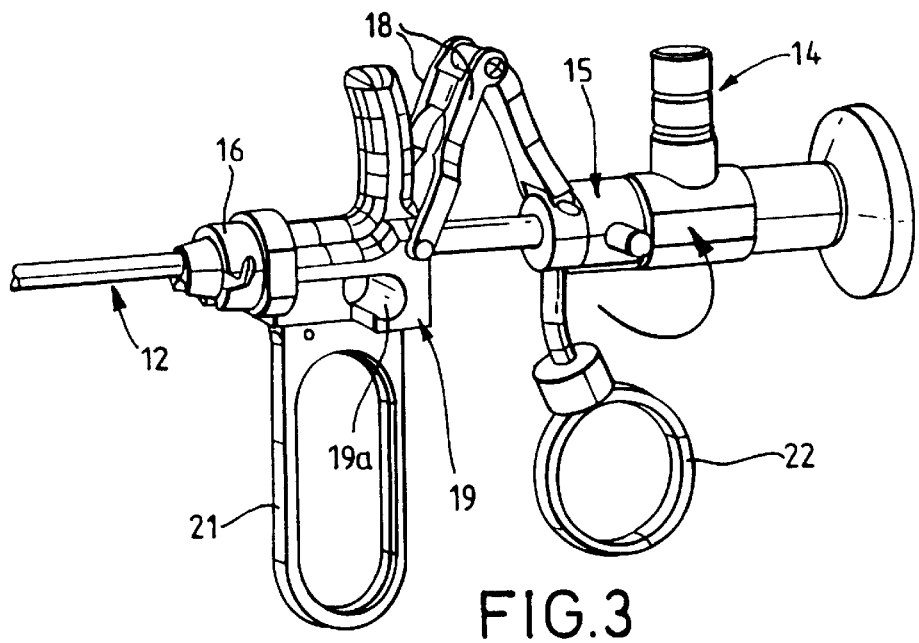
FIG. 3 is an enlarged perspective view of the proximal end portion of the resectoscope shown in FIGS. 2A to 2C.

The electrode assembly 13 may be either passive or active, that is to say the cutting stroke of the electrode may be as a result of a spring bias or against the force of a spring bias. The telescope tube 12 has a rotatable locking collar 15 (see FIG. 3) at its proximal end adjacent to the connector 14, the locking collar being rotatable relative to the telescope tube for locking/unlocking thereto. A sealing block 16 is located part way along the telescope tube 12, the inner sheath 1 being connected to the sealing block. Both of these interfaces are watertight. Two spring-loaded links 18 and a PTFE mounting block 19, located between the sealing block 16 and the telescope locking collar 15, make up the mechanism. The active mechanism is arranged so that the spring-loaded links 18 assist the forward stroke, while, in the passive version, the links aid the backward stroke. In general, the range of travel is about 25 mm.

Figure 4:
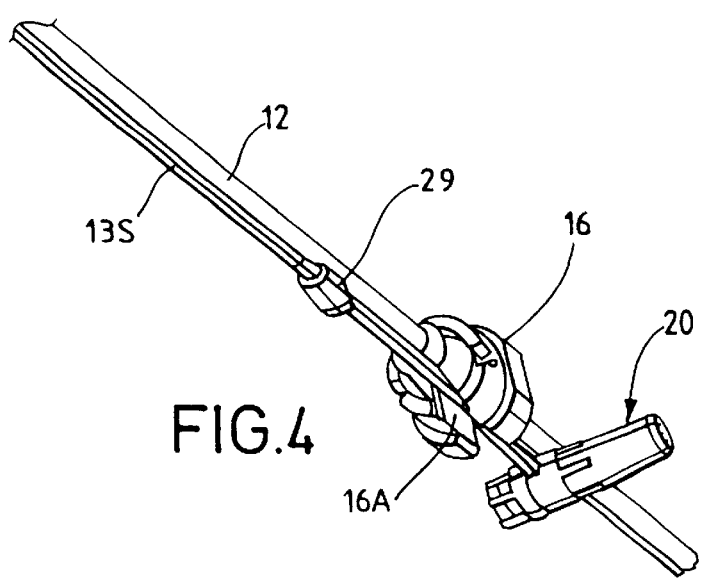
FIG. 4 is an enlarged perspective view of an intermediate portion of the resectoscope shown in FIGS. 2A to 2C.

At their proximal ends, the conductors of the support structure 13S enter an insulative cable-mounting block 20 (see FIG. 4) which, when the instrument is assembled, is housed in a groove 19a (see FIG. 4) in the mounting block 19, as shown in FIGS. 2B and 2C. As shown in FIGS. 2A and 4, the proximal end portion of the support structure 13S is bent, at a small angle, out of alignment with the main portion of the support structure. This feature ensures that the cable-mounting block 20, which is relatively large, can be adequately supported by the mounting block 19.

This mounting block 19 is slidable on the telescope tube 12 with respect to the locking collar 15, relative movement between the mounting block and the locking collar being effected by squeezing together two handles 21 and 22 attached thereto. As a result, the distal tip assembly 13T can be reciprocated relative to the end of the telescope tube 12. Inside the block 20, connections are made (as is described below) between the conductors of the support structure 13S and a flexible cable 23 which is terminated in an in-line connector 24 for connecting the instrument to an electrosurgical radio frequency generator (not shown). The conductors of the support structure are insulation-coated, spring steel wires 25 and 26.

Figure 5:
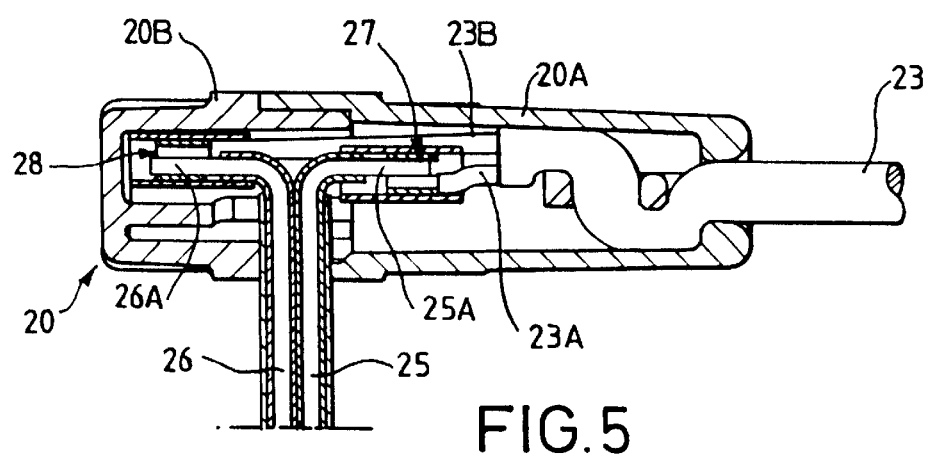
FIG. 5 is an enlarged sectional view of a cable-mounting block forming part of the arrangement shown in FIG. 4.

The in-line connector 24 can be an IP64 rated in-line connector, or better, which reduces a potential failure mode by moving the electrode connection away from the telescope tube 12 without having to bend a rigid member such as the electrode support tube 7 of the prior art resectoscope. Thus, as shown in FIG. 5, the proximal end portions of the two spring steel wires 25 and 26 enter a two-part housing 20A, 20B of the block 20 from the side, the housing being made of an electrically-insulating material such as a thermoplastics material. Within the housing 20A, 20B, the wires 25 and 26 bend away from one another through 90°, the free end portions of 25A and 26A of the wires being electrically connected to wires 23A and 23B of the flexible cable 23 by means of respective connectors 27 and 28. Once the electrical connections are made, the two housing parts 20A and 20B are sonic welded together to form a completely sealed unit.

In order to seal the support structure 13S, to prevent fluid flowing away from an operation site towards the block 20, a shaft seal 29 is fixed to the support structure adjacent to its proximal end. As shown in FIG. 4, the shaft seal 29, which is made of natural or synthetic rubber, is of tapered construction so that the seal 29 is positioned and locked within a complementary slot 16A formed in a sealing block 16 by engagement with the inner sheath 11. The electrode assembly 13 is subsequently movable longitudinally relative to the seal 29, whilst ensuring good watertight sealing against fluid flow along the support structure 13S from an operation site adjacent to the electrode tip 13T towards the cable-mounting block 20. The electrode assembly 13 is designed for single use, so that the shaft seal 29 is not subjected to a significant amount of wear, making this sealing method far more reliable than that of the prior art. Moreover, the need for the seal 29 to have an adjustment feature is removed, reducing the variation in frictional resistance from one electrosurgical procedure to the next.

In order to assemble the resectoscope, the electrode assembly 13 is fixed to the block 20 by connecting the end portions 25A and 26A of the conductor wires 25 and 26 to the wires 23A and 23B via the connectors 27 and 28. The entire electrode assembly 13 is then secured to the telescope assembly (that is to say the telescope tube 12 and the associated sealing block 16, mounting block 19 etc) by inserting the cable-mounting block 20 into the groove 19A and rotating the electrode assembly to bring the shaft seal 29 firmly into engagement with the slot 16A, thereby holding the support structure 13S in position, and sealing it against the sealing block 16. The clip, 13C mounted near the distal end of the support structure 13S then locks onto the telescope tube 12 to maintain this orientation. The loading of the shaft seal 29 into the slot 16A in the sealing block 16 restricts lateral movement of the electrode assembly 13, but permits relative longitudinal movement.

The shaft seal 29 is automatically located into the slot 16A when the electrode assembly 13 is subsequently introduced into the inner sheath 11 (see FIG. 2B). This is achieved by the seal 29 wedging within the slot 16A, which allows for any slight misalignment as the seal is pushed into the slot. Moreover, the automatic loading of the seal 29 ensures that it is always correctly seated, and greatly simplifies loading procedure. Furthermore, as the seal 29 fills the slot 16A, the integrity of the interface between the inner sheath 11 and the sealing block 16 is maintained.

A final stage of instrument assembly, not shown in the drawings, consists of the fitting of the outer sheath (not shown) around the inner sheath 1, to mate with the sealing block 16.

What is claimed is:

1. An endoscope comprising a telescope, an electrode assembly comprising at least one electrode and elongate conductive means for supplying electrosurgical power to said at least one electrode from the proximal end of the conductive means, mounting means for supporting the electrode assembly on the telescope for pivotal movement, in a plane substantially normal to the axis of the telescope, towards, and away from, an operational position in which the conductive means is substantially parallel to the telescope, and sealing means for sealing the electrode assembly to prevent fluid passing from an operation site adjacent to said at least one electrode to the proximal end of the conductive means.

2. An endoscope as claimed in claim 1, wherein the sealing means is constituted by a seal attached to the conductive means, and a sealing block associated with the telescope, the sealing block being formed with a slot for receiving the seal.

3. An endoscope as claimed in claim 2, wherein the seal has the tapering cross section, and the slot in the sealing block is of complementary shape, whereby the seal forms a sliding friction fit within the slot of the sealing block, whereby said at least one electrode is movable longitudinally relative to the seal, whilst ensuring good watertight sealing against fluid flow towards said proximal end of the conductive means.

4. An endoscope as claimed in claim 1, wherein the electrode assembly comprises a tissue treatment electrode and a return electrode, and the elongate conductive means is constituted by a pair of conductors.

5. An endoscope as claimed in claim 4, wherein each of the conductors is an insulation-coated, spring steel conductor.

6. An endoscope as claimed in claim 4 wherein the proximal ends of the conductors terminate in an electrical connector.

7. An endoscope as claimed in claim 6, wherein the electrical connector includes electrical connection means for connecting the conductors to an electrosurgical generator by a flying lead and an in-line connector.

8. An endoscope as claimed in claim 6, wherein the electrical connector is a watertight unit.

9. An endoscope as in claim 6 wherein the mounting means includes a mounting block associated with the telescope, and means fixed to the electrode assembly for engagement with the mounting block; and wherein the mounting block is formed with a curved recess for receiving a complementary curved surface of the electrical connector, whereby the electrical connector is rotatable relative to the mounting block so that the electrode assembly can be pivoted into its operational position.

10. An endoscope as claimed in claim 1, wherein the mounting means includes a mounting block associated with the telescope, and means fixed to the electrode assembly for engagement with the mounting block.

11. An endoscope as claimed in claim 9, wherein the mounting means further comprises a clip fixed to the conductive means at the distal end portion thereof the clip being adapted for engagement with the distal end portion of the telescope.

* * * * *